(12) United States Patent
Yamazaki

(10) Patent No.: US 7,901,350 B2
(45) Date of Patent: Mar. 8, 2011

(54) ADAPTER UNIT FOR CONNECTING CLEANING FLUID SUPPLY DEVICE TO ENDOSCOPES

(75) Inventor: Masayuki Yamazaki, Saitama (JP)

(73) Assignee: Fujinon Corporation, Saitama-Shi (JP)

( * ) Notice: Subject to any disclaimer, the term of this patent is extended or adjusted under 35 U.S.C. 154(b) by 187 days.

(21) Appl. No.: 11/289,437

(22) Filed: Nov. 30, 2005

(65) Prior Publication Data

US 2006/0135851 A1    Jun. 22, 2006

(30) Foreign Application Priority Data

Nov. 30, 2004    (JP) ................................. 2004-345806

(51) Int. Cl.
*A61B 1/12* (2006.01)
*A61B 1/04* (2006.01)
*A61B 1/00* (2006.01)

(52) U.S. Cl. ........................................ 600/159; 133/152
(58) Field of Classification Search .................. 600/118, 600/152, 153, 155, 156, 158, 159, 133, 154
See application file for complete search history.

(56) References Cited

U.S. PATENT DOCUMENTS

| | | | | |
|---|---|---|---|---|
| 3,198,483 A | * | 8/1965 | Anderson | 251/327 |
| 4,241,761 A | * | 12/1980 | Miller | 137/883 |
| 4,637,378 A | * | 1/1987 | Sasa | 600/155 |
| 5,247,966 A | * | 9/1993 | Stevens et al. | 137/625.69 |
| 5,697,888 A | * | 12/1997 | Kobayashi et al. | 600/159 |
| 6,383,132 B1 | * | 5/2002 | Wimmer | 600/159 |
| 6,797,245 B2 | * | 9/2004 | Nakanishi et al. | 422/300 |
| 2005/0065405 A1 | * | 3/2005 | Hasegawa | 600/158 |

FOREIGN PATENT DOCUMENTS

| | | | |
|---|---|---|---|
| EP | 71058 A2 | * | 2/1983 |
| JP | 2001-278692 | | 10/2001 |

* cited by examiner

*Primary Examiner* — Linda C Dvorak
*Assistant Examiner* — Alireza Nia
(74) *Attorney, Agent, or Firm* — Young & Thompson

(57) ABSTRACT

A cleaning adapter unit for connecting a cleaning fluid supply device to different type endoscopes comprises adapter valve assemblies which correspond to the different endoscopes, respectively. Each adapter valve assembly comprises a valve sleeve detachably connectable to the cleaning fluid supply device and a valve body received in the valve sleeve for slide movement and forming a valve chamber leading to the passage in the valve sleeve. The valve sleeve has a passage and is provided with a first fitting at one end thereof which is formed so as to be hermetically received in a valve casing of one of the different endoscopes, and the valve body is provided with first and second passages formed separately therein and opens at opposite ends, respectively, and with a second fitting at one ends thereof opposite to the one end of the valve sleeve at which the first fitting is formed so as to be hermetically received in the valve casing of the other different endoscope. The valve body brings the passage into communication with the first passage through the valve chamber when the cleaning adapter unit is attached to the one different endoscope by fitting the first fitting in the valve casing of the endoscope and with the second passage through the valve chamber when attached to the other endoscope by fitting the second fitting in the valve casing of the endoscope.

11 Claims, 6 Drawing Sheets

ADAPTER UNIT FOR CONNECTING CLEANING FLUID SUPPLY DEVICE TO ENDOSCOPES

BACKGROUND OF THE INVENTION

1. Field of the Invention

The present invention relates to a cleaning adapter unit for connecting an accessorial cleaning device to a medical endoscope having a fluid conduit and, more specifically, to an accessorial cleaning device cleaning adapter unit for detachably connecting an accessorial cleaning device for delivering a chemical into fluid conduits of a medical endoscope through fluid valves.

2. Description of Related Art

Endoscopes for, in particular, medical application have a plurality of conduits opening at a distal end of an insertion pait. Typical example of the conduits is an insertion channel for introducing medical instruments such as a forceps into a body cavity for picking of body tissues or a medical treatment of affected parts. Such a medical endoscope is provided with an observation window at a distal end of the insertion part. When the window is tainted with a body fluid, it is necessary to wash out the body fluid from the window with water and pressurized air that is supplied through an air/water tube and sprayed from a nozzle so as thereby to keep the window clean sufficiently enough to provide a clear vision. The medical endoscope is further provided with a suction tube through which filthy matters are sucked out of a body cavity. Generally, this suction tube is not always provided independently and partly combined with the instment insertion channel. The instrument insertion channel extends from an instrument inlet formed in a control section of the endoscope, and the suction tube out of the endoscope branches off from the instrument insertion channel and extends within a sheath tube of universal cords to a suction unit. Some kinds of endoscopes are further provided with one or more auxiliary injection passages.

Among these tubes and passages, the air/water tube is controlled by a fluid control valve assembly installed in the control section of the endoscope. The fluid control valve assembly comprises an air/water feed valve and a suction valve. These valves are an arranged adjacently to each other as closely as possible for easy operation with fingers of an operator's hand gripping on the control section of the endoscope. Each of the valves has a valve body mounted in a valve casing of the endoscope to which the relevant tube or passage is connected and an operating button installed to the control section of the endoscope so as to extend out of the endoscope for easy operation of the surgical operator.

In the above circumstances, it has been proposed in, for example, Unexamined Japanese Patent No. 6-6103 to use a cleaning adapter unit attachabe to the control section where the air/water feed valve, the suction valve and the operating buttons have been uninstalled in order to make it possible to wash an interior of the air/water tube and an interior of the suction passage. According to the cleaning adapter unit, when removing these valves and buttons, the valve casing appears out of the control section. The valve casing has a mounting flange to which the operating buttons and the cleaning adapter unit are interchangeably attached.

These air/water feed valve and a suction valve are structured so that valve bodies and their associated operating buttons are removed from valve casings. However, the valve casings are not always structurally identical, more specifically different in shape and dimensions according to types of endoscopes. Consequently, when cleaning different types of endoscopes, it is essential to prepare various types of adapters different in shape and dimensions correspondingly to respective types of the valve casings of different endoscopes. This is undesirable from the viewpoint of a large storage space for various types of adapters and identification of the adapters according to types of the valve casings.

SUMMARY OF THE INVENTION

It is therefore an object of the present invention to provide a cleaning adapter unit for use with endoscopes having different types of fluid control valves such as air/water feed valve and a suction valve. The aforesaid object of the present invention is accomplished by a cleaning adapter unit for connecting cleaning fluid supply means selectively to types of endoscopes equipped with fluid control valve means, respectively, different from each other each of which comprise a valve casing fixedly installed in a control section of the endoscope and connected to at least one conduit extending within the endoscope and a valve body removably received in the valve casing so that cleaning fluid is supplied into the conduit from the cleaning fluid supply means though the cleaning adapter unit for cleaning an interior of the conduit. The cleaning adapter unit comprising an adapter valve sleeve having an inlet fluid passage detachably connectable to the cleaning fluid supply means and provided with first fitting means at one of opposite ends thereof, the first fitting means being formed so as to be hermetically received in the valve casing of one of the different type endoscopes, and an adapter valve body received in the adapter valve sleeve for slide movement and forming a valve chamber leading to the inlet fluid passage in the adapter valve sleeve, the adapter valve body being provided with first and second fluid passages formed separately from each other therein and opening at opposite ends thereof, respectively, and provided with second fitting means at one of opposite ends thereof opposite to the one end of the adapter valve sleeve at which the first fitting means is formed so as to be hermetically received in the valve casing of the other of the different type endoscope, wherein the adapter valve body brings the inlet fluid passage into communication with the first fluid passage through the valve chamber when the cleaning adapter unit is attached to one of the different type endoscopes by fitting the first fitting means in the valve casing of the one of the different type endoscopes and, on the other hand, with the second fluid passage through the valve chamber when the cleaning adapter unit is attached to the other of the different type endoscopes by fitting the second fitting means in the valve casing of the other of the different type endoscopes.

The cleaning adapter unit is used to connect conduits extending an endoscope to a chemical supply device for supplying cleaning chemicals such as antisepfic solutions, sterilant solutions, cleaning liquids, etc. into the conduits for sterilization of interiors of the conduits. The chemical supply device comprises a chemical deed tube, a chemical feed pump, a syringe, and other constituent parts. The cleaning adapter unit is connected, on one hand, to the chemical supply device through the chemical introduction port thereof and, on the other hand, to the valve casing of an endoscope from which a fluid control valve and its associated operating button are removed, through the first fluid passage or the second fluid passage thereof. Therefore, the cleaning adapter unit is capable of selectively connecting the chemical supply device to two types of endoscopes having valve casings different in shape and dimensions from each other.

The fluid control valve of an endoscope to which the cleaning adapter unit is connected is not specifically limited by type and number and typical endoscopes are provided with an air/water feed valve and a suction valve. Accordingly, the cleaning adapter unit should be of a type of being detachably connectable to an endoscope having these two fluid control valves. These air/water valve and suction valve installed to typical endoscopes are closely arranged side by side so as to be easily operated by fingers of an operator's hand Therefore, the adapter valve sleeves for these air/water feed valve and suction valve may be desirably coupled side by side as one whole unit by coupling means. The coupling means may comprise a coupling frame for fixedly coupling the adapter valve sleeves side by side, a stopper cover having a hole greater than a diameter of the sleeve section and slidably attached to the coupling frame, and biasing means, such as a coil spring or a rubber, disposed between the coupling frame and the stopper cover for biasing the stopper cover in a direction in which the stopper cover is brought into engagement with the sleeve section of the fluid control valve means at an edge of the hole.

BRIEF DESCRIPTION OF THE DRAWINGS

The foregoing and other objects and features of the present invention will be clearly understood frame the following detailed description when reading with reference to the accompanying drawings, wherein the same reference signs have been used to denote same or similar parts throughout the drawings, and in which.

DETAILED DESCRIPTION OF THE PREFERRED EMBODIMENTS

Figure 1:
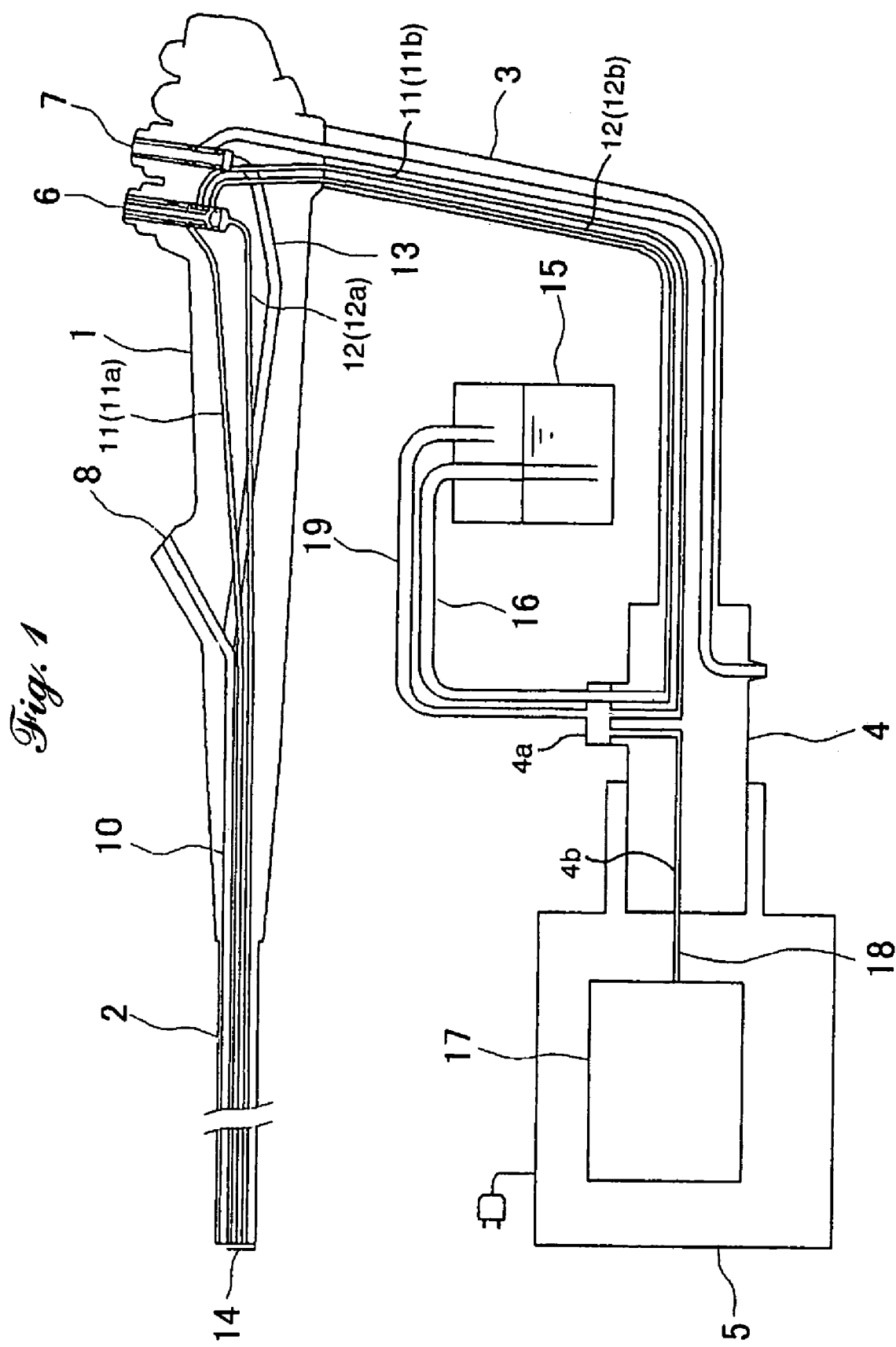
FIG. 1 is a schematic view of a conduit arrangement of an endoscope.

Referring to the accompanying drawings in detail, and, in particular, to FIG. 1 schematically showing a conduit arrangement of an medical endoscope 100, the endoscope 100 comprises a control section 1, a flexible insertion section 2 extending from the control section 1, and an universal cord 3 extending from the control section 1 and a connector 4 fixed to a distal end of the universal cord 3. The universal cord 3 is detachably connected to a control device 5 including a light source unit, an image processor unit, a pump, etc. therein. The control section 1 is provided with an air/water valve 6 and a suction valve 7 mounted thereto and has an instrument inlet 8 formed near the insertion section 2. The conduits typically include at least an instrument channel 10 such as a foicepss channel, an air supply tube 11, a water supply tube 12 and a suction tube 13. The instrument channel 10 extends from the instrument inlet 8 and opens out at a distal end of the insertion section 2. The air supply tube 11 comprises two half sections, namely a first half section extending within the control section 1 to the distal end of the insertion section 2 and the insertion section 2 and a second half section extending within the universal cord section 3 to the connector 4, which are connected to each other though the air/water valve 6. Similarly, the water supply tube 12 comprises two half sections, namely a first half section extending within the control section 1 and the insertion section 2 to the distal end of the insertion section 2 and a second half section extending within the universal cord section 3 to the connector 4, which are connected to each other through the suction valve 7. The first halves of the air supply tube 11 and the water supply tube 12 lead, separately or partially in one united body, to a nozzle 14 directed to an observation window (not shown). The suction tube 13 comprises two half sections, namely a first half section extending within the control section 1 to the instrument channel 10 in vicinity of the instrument fluid introduction inlet 8 and a second half extending within the universal cord section 3 to the connector 4, which are connected to each other through the suction valve 7. The second half section of the water supply tube 12 terminates in close vicinity of the air chamber 4a in the connector 4, and the second half of the suction tube 13 terminates and opens to the atmosphere at one side of the connector 4. The connector 4 has an air chamber 4a and an air channel 4b extending from the air chamber 4a to an end section of the connector 4.

The control device 5 with an air pump 17 installed therein has a socket 5a through which the connector 3 is connectable to the control device 5. When the connecter 3 is connected to the control device 5, the air channel 4a is connected to the air pump 17. A water tank 15 is provided with a water supply tube 16 connectable to the air chamber 4a of the connector 4 and an air supply tube 19 connectable directly to an end of the water supply tube 12 of the endoscope. When the air pump 17 is activated, the air chamber 4a of the connector 4 is filled with air fed by the air pump 17. The air is forced partly into the interior of the water tank 15 and partly into the air supply tube 11. Then, the interior of the water tank 15 is filled with the air fed through the air supply tube 19, so that water in the water tank 15 is compressed by the air and forced to flow through the water supply tube 16.

These air/water valve 6 and suction valve 7 are equipped with fluid control valve mechanisms, respectively, that are different in mechanism and sizes according to types of endoscope and, however, generally common to conduits in spite of types of endoscope. The following description will be directed to typical fluid control mechanisms.

Figure 2:
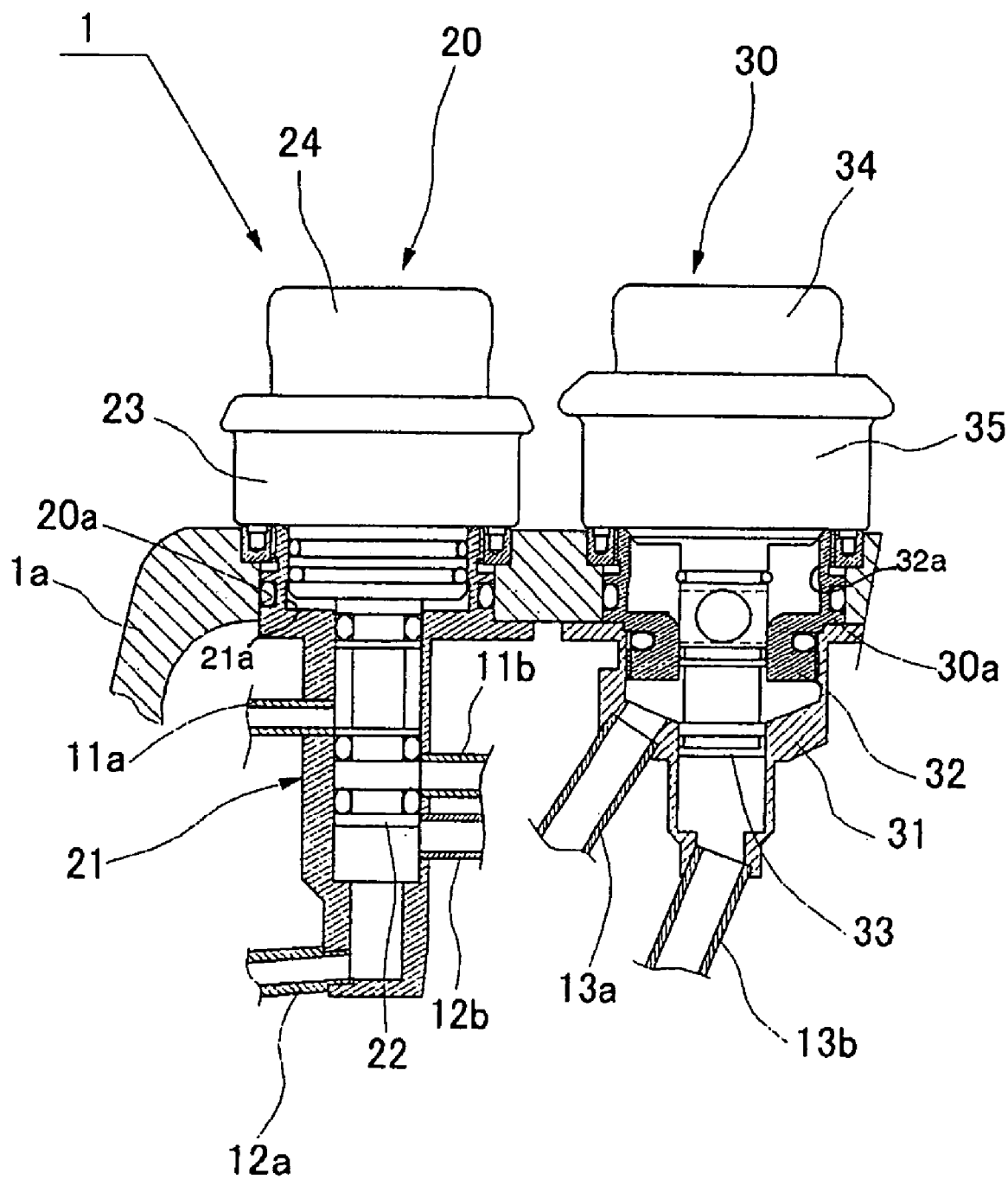
FIG. 2 is a sectional view of an air/water valve and a suction valve of one type of endoscope.

FIG. 2 shows details of an example of air/water valve 20 and suction valve 30 capable of being detachably attached to the control section 1 of the endoscope shown in FIG. 1. The control section 1 has a housing 1a having valve sockets 20a and 30a formed therein. A valve casing 21 is fixedly received in the valve socket 20a and extending partly in the housing 1a of the control section 1 and partly within the valve socket 20a. The air supply tube 11, namely an upstream tube section 11b extending within the universal cord 3 and a downstream tube section 11a extending mainly within the insertion section 2, are connected to the valve casing 21. Similarly, the water supply tube 12, namely an upstream tube section 12b extending within the universal cord 3 and a downstream tube section 12a extending mainly within the insertion section 2, are connected to the valve casing 21. A valve casing 31 is entirely positioned within and fixed to the housing 1a of the control section 1. The suction tube 13, namely an upstream tube section 13b extending within the universal cord 3 and a downstream tube section 13a extending mainly within the insertion section 2, are connected to the valve casing 31.

Both air/water valve 6 and the suction valve 7 are detachably put in the control section 1 of the endoscope. The air/water valve 20 comprises a valve body assembly 22 extending within and hermetically guided by the valve casing 21, a valve guide 23 seated above an enlarged section, i.e. a valve mount 21a, of the valve casing 21, and a valve operating button 24 to which the valve body assembly 22 is fixed. These valve elements 22, 23 and 24 are formed so as to be capable of being put in and taken off out of the valve casing 21 as one united body. The suction valve 30 comprises a valve guide sleeve 32 fixedly connected to the valve casing 31 and fixedly installed within the valve socket 30a, a valve body assembly 33 extending within and hermetically guided by the valve guide sleeve 32, a valve casing 31, a valve guide 35 seated above an enlarged section, i.e. a valve mount 32a, of the valve guide sleeve 32, and a valve operating button 34 to which the valve body assembly 33 is fixed. The valve body assembly 33 has an enlarged section for hermetic guide by the valve guide sleeve 32. The valve guide sleeve 32 has an enlarged valve mount 31a. The valve body assemblies 22 and 33 are formed so as to be capable of being put in and taken off out of the valve casing 21 and the valve guide sleeve 32 as one united bodies, respectively.

Figure 3:
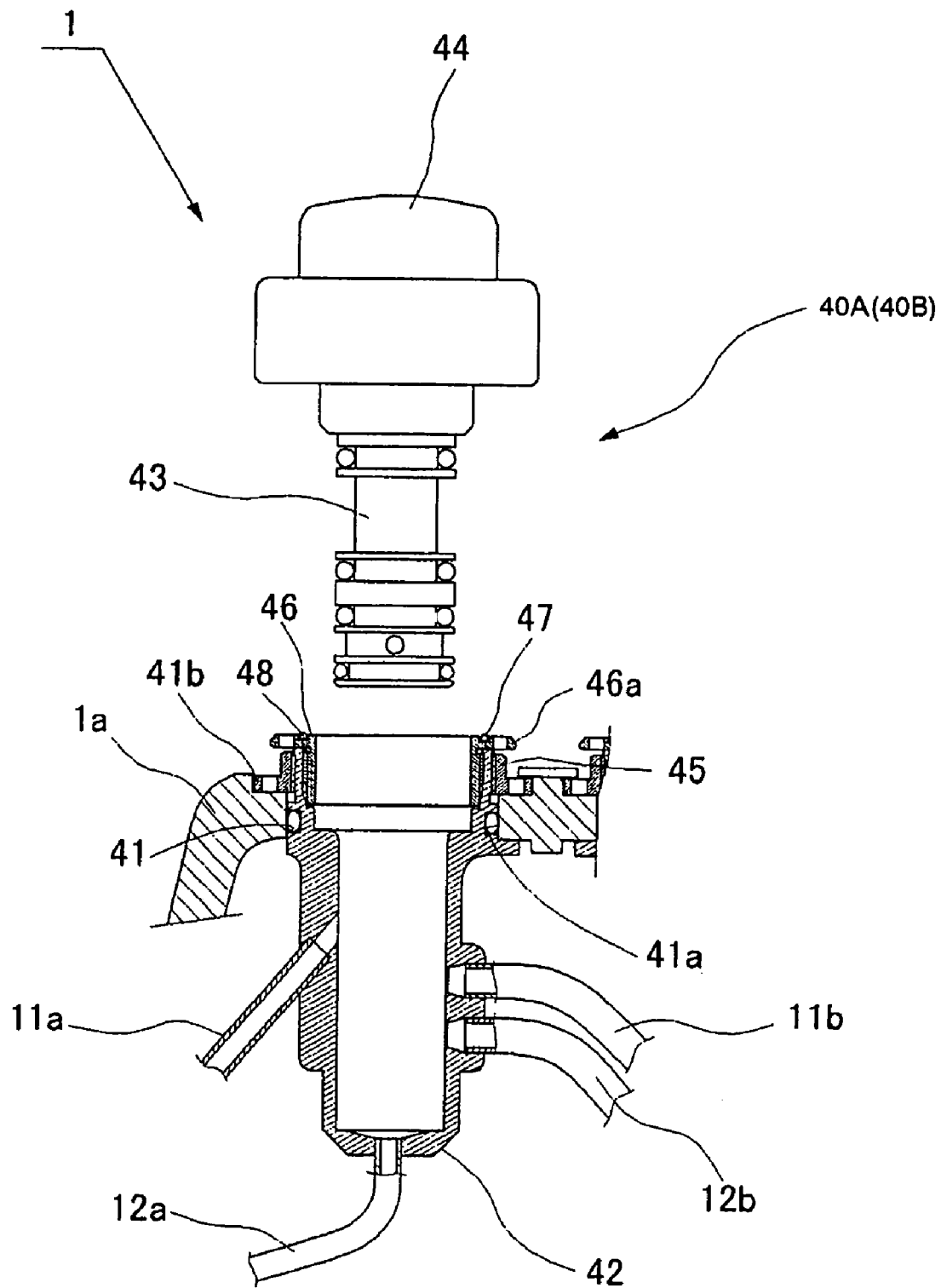
FIG. 3 is a sectional view of a valve casing with an air/water valve removed of another type of endoscope.

FIG. 3 shows details of another example of an air/water valve and a suction valve capable of being detachably attached to the control section 1 of the endoscope shown in FIG. 1. In this example, these air/water valve and suction valve are equipped with the same fluid control valve mechanisms, the following description will be directed to an air/water valve 40A only, and a suction valve is parenthetically shown only as a reference sign 40B in FIG. 3. The air/water valve 40A comprises a valve casing 42 fixedly received in a valve socket 41 formed in the housing 1a of the control section 1 of the endoscope shown in FIG. 1, a valve body assembly 43 hermetically received within the valve casing 42, and a valve operating button 44 to which the valve body assembly 43 is fixed. The valve socket 41 comprises two socket sections, namely a base socket section 41a in which the valve casing 42 is hermetically fitted and an enlarged socket section 41b in which a union nut 45 forming an external side wall section of the valve casing 42 is fixedly received for screw-in connection of the valve casing 42, and a flanged valve mount 46 screwed in the valve casing 42 so as to form a sleeve section extending out of the control section 1. The valve body assembly 43 and the valve operating button 44 are formed as one integral piece. The flanged valve mount 46 is provided with a sealing W ring 47 seated in an annular groove 48 formed in a flange 46a thereof so as to built up hermetic seal sealing of the interior of the valve casing 42. The suction valve (not shown) has the same structure as the air/water valve 44.

Figure 4:
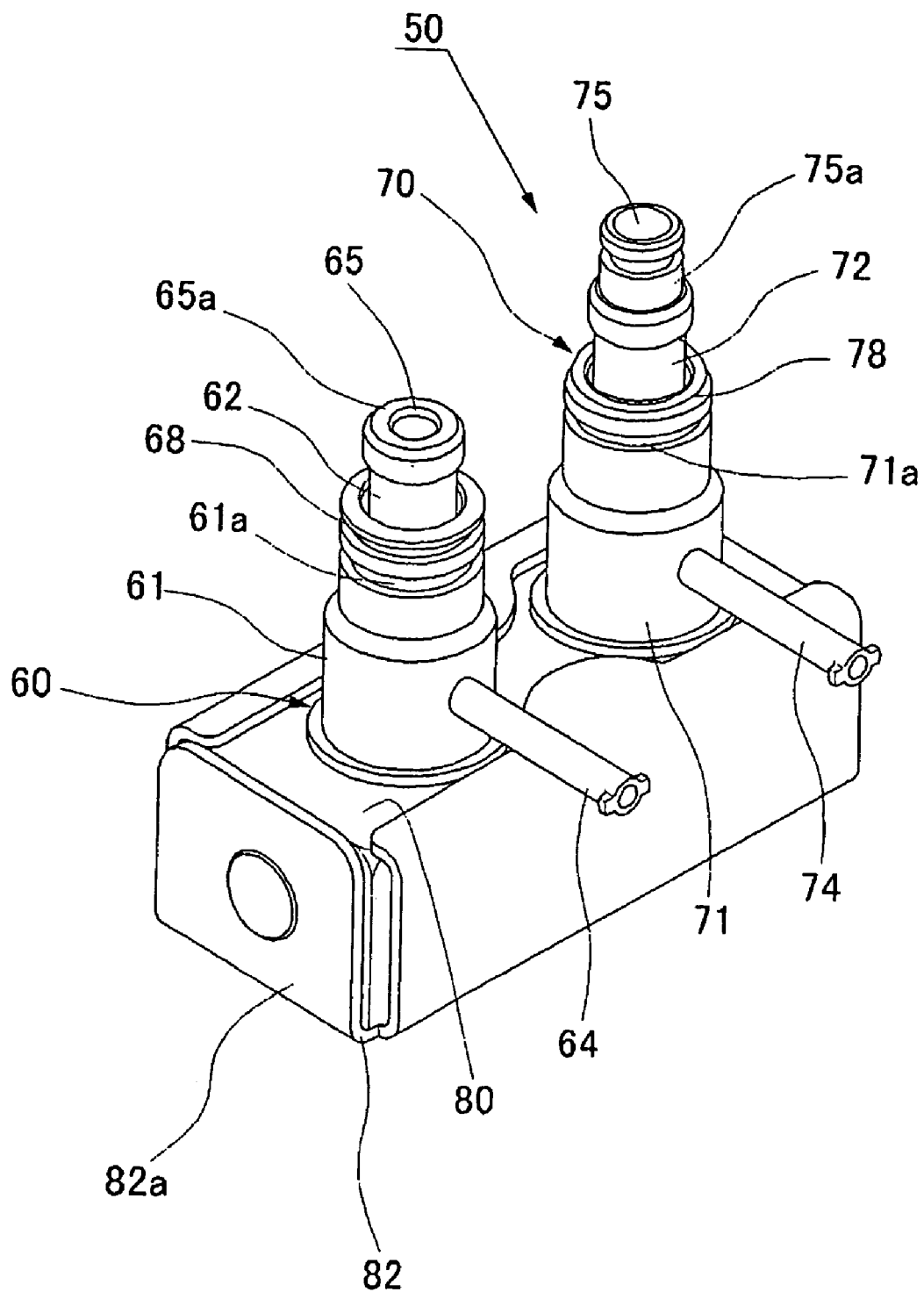
FIG. 4 is a perspective view of a cleaning adapter unit according to an embodiment of the present invention.

FIG. 4 shows a cleaning adapter unit 50 capable of being attached to and detached from the endoscope equipped with either the air/water valve 20 and the suction valve 30 shown in FIG. 2 or the air/water valve 40A and the suction valve 40B shown in FIG. 3. The cleaning adapter unit 50 is connected to a cleaning device (not shown) through fluid introduction pipes 64 and 74 as a fluid introduction ports. Cleaning chemical fluids, the same as or different from each other, are introduced into the valve chambers 63 and 73 of the adapter spigots 60 and 70, respectively, from the cleaning device through the fluid introduction pipes 64 and 74, respectively. The cleaning adapter unit 50 has a pair of adapter spigots 60 and 70 fixedly mounted to a box-shaped coupling flame 80. As shown more specifically in FIGS. 5 and 6, the adapter spigot 60 comprises a substantially cylindrical valve sleeve 61 and a valve body 62 which is hermetically received in the valve sleeve 61 so as to make axially up and down slide movement. The valve sleeve 61 has an enlarged intermediate section in an axial span of specified length. On the other hand, the valve body 62 has a wasp intermediate section in an axial span of a specified length shorter than the corresponding section of the valve sleeve 61. Therefore, there is formed a generally cylindrical space as a valve chamber 63 in the adapter spigot 60 between the valve sleeve 61 and the valve body 62. The adapter spigot 60 is provided with the fluid introduction pipe 64 leading to the valve chamber 63 in a direction perpendicular to the axis line of up and down movement of the valve body 62. The valve body 60 has a second passage 65 and a third passage 66 formed therein and opening at opposite ends thereof so as to bring the valve chamber 63, and hence a first passage formed by the fluid introduction pipe 64, into communication with the atmosphere selectively through the second and third passages 65 and 66. The valve body 60 is provided with a passage sleeve 65a inserted into the third passage 65. For reliable disconnection of the valve chamber 63 with the passage 65 or 66, the valve body 62 is provided with sealing rings 67a and 67b near the re red intermediate section thereof Similarly, the adapter spigot 70 comprises a substantially cylindrical valve sleeve 71 and a valve body 72 which is hermetically received in the valve sleeve 71 so as to make axially up and down slide movement axially movable up and down. The valve sleeve 71 has a enlarged intermediate section in an axial span of specified length. The valve body 72 has a wasp intermediate section in an axial span of a specified length shorter than the corresponding section of the valve sleeve 71. Therefore, there is formed a generally cylindrical space as a valve chamber 73 in the adapter spigot 70 between the valve sleeve 71 and the valve body 72. The adapter spigot 70 is provided with the fluid introduction pipe 74 leading to the valve chamber 73 in a direction perpendicular to the axis line of up and down movement of the valve body 72. The valve body 70 has a second passage 75 and a third passage 76 formed therein and opening at opposite ends thereof so as to bring the valve chamber 73, and hence a fit passage formed by the fluid introduction pipe 74, into communication with the atmosphere selectively through the second and third passages 67 and 76. The valve body 70 is provided with a passage sleeve 75a inserted into the third passage 75. For reliable disconnection of the valve chamber 73 with the passage 75 or 76, the valve body 72 is provided with sealing rings 77a and 77b near the re red intermediate section thereof The valve sleeve 61 at one of opposite ends has a hermetical fitting end section 68 provided with a pair of sealing rings 61a. On the other hand, the valve body 61 at one of opposite ends has a hermetical fitting end section 69 enlarged in external diameter and in which the third passage 66 is formed and which is provided with a sealing ring 62a. Similarly, the valve sleeve 71 at one of opposite ends has a hermetical fitting end section 78 provided with a pair of sealing rings 71a, and the valve body 71 at one of opposite ends has a hermetical fitting end section 79 enlarged in external diameter and in which the third passage 76 is formed and which is provided with a sealing ring 72a. In this instance, the fitting end sections 68 and 78 of the valve sleeves 61 and 71 of the body the adapter spigots 60 and 70, respectively, are shaped so as to be snugly fitted in the valve mount 21a and 33a of the valve casings 21 and 31 of the air/water valve 20 and the suction valve 30 (shown in FIG. 2), respectively. On the other hand, fitting end sections 69 and 79 of the valve bodies 62 and 72 of the adapter spigots 60 and 70, respectively, are shaped so as to be snugly fitted in the valve mount 46, different in size and/or shape from the valve mounts 21a and 33a, air/water valve 40A and the suction valve 40B (shown in FIG. 3).

Figure 5:
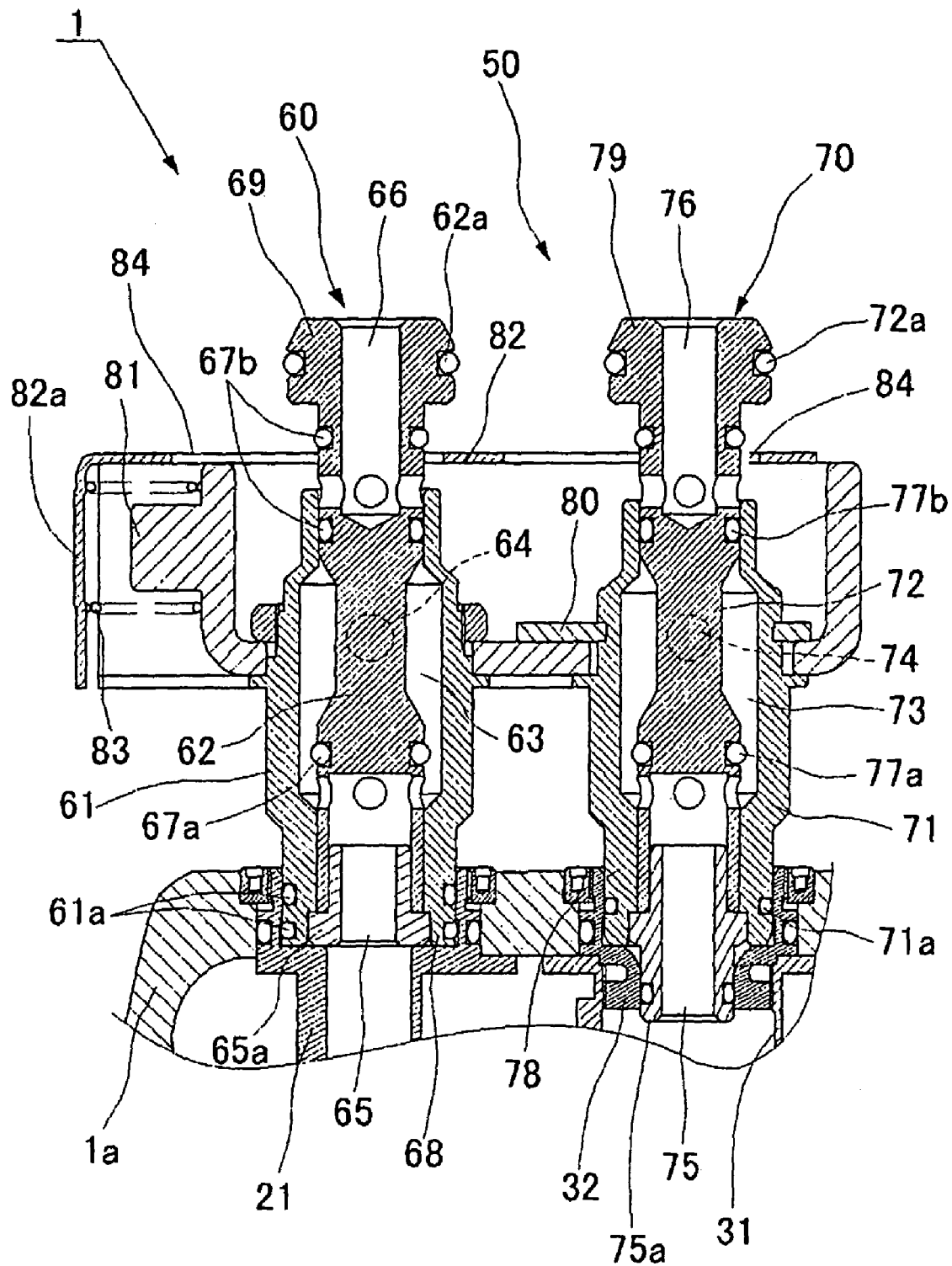
FIG. 5 is a sectional view of the cleaning adapter unit connected to the endoscope shown in FIG. 2.
Figure 6:
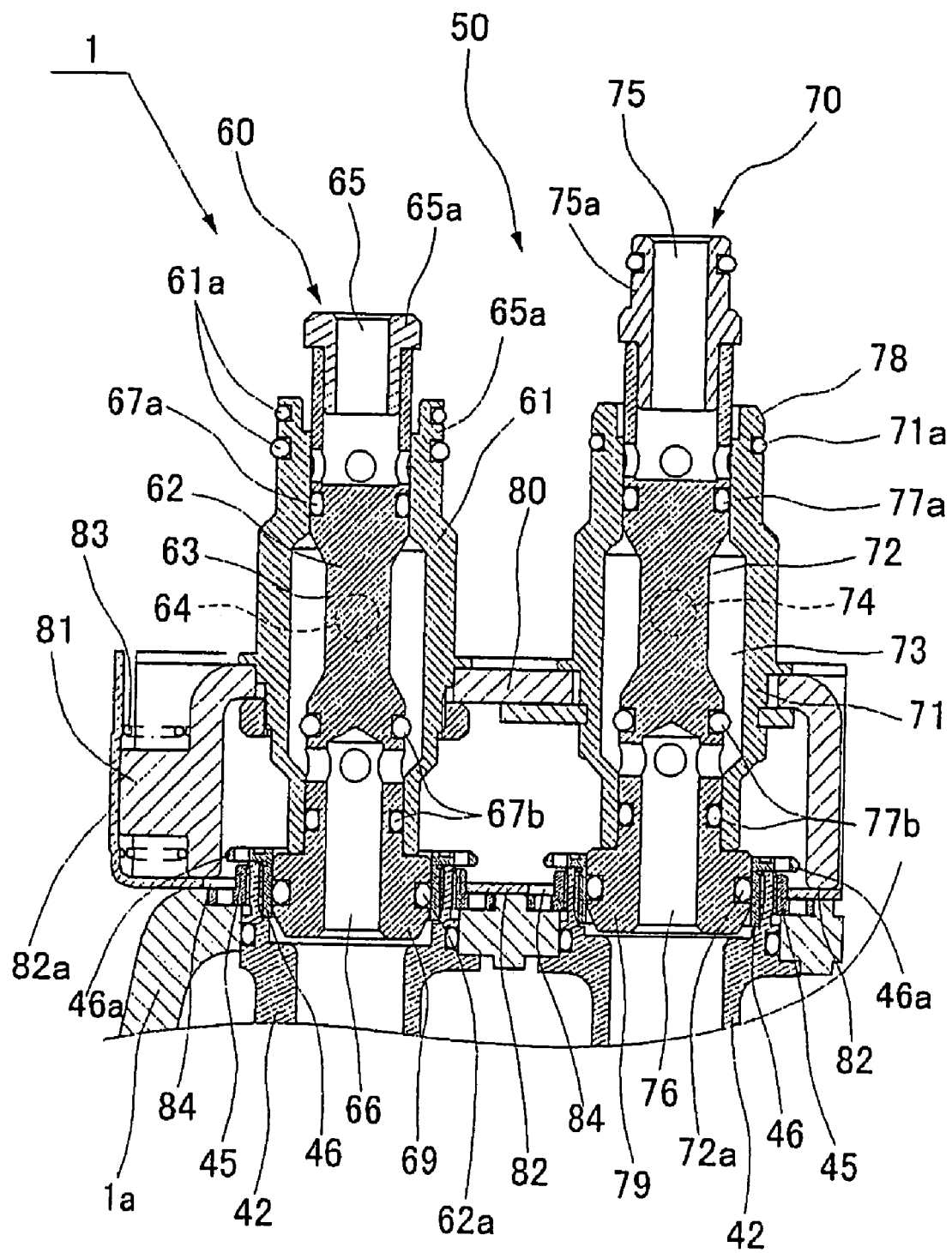
FIG. 6 is a sectional view of the cleaning adapter unit connected to the endoscope shown in FIG. 3.

The valve body 60, 70 and the valve sleeve 61, 71 are allowed to cause relative slide movement between a first position where the other end of the of the valve sleeve 61, 67 abuts against a shoulder of the passage sleeve 65a, 75a as shown in FIG. 5 and a second position where one of opposite ends of the valve sleeve 61, 71 abuts against a shoulder of the hermetical fitting end section 69, 79 (see FIG. 6). In the second position shown in FIG. 5, the first passage (the fluid introduction pipe 64, 74) of each adapter spigot 60, 70 is brought into communication with the second passage 65, 75 through the valve chamber 63, 74 but shut off from the third passage 66, 76 by means of hermetical contact of the sealing ring 67b, 77b with the inner wall of the valve sleeve 61, 71. On the other hand, in the first position shown in FIG. 6, the first passage (the fluid introduction pipe 64, 74) of the adapter spigot 60, 70 is brought into communication with the third passage 66, 76 through the valve chamber 63, 74 but shut off from the second passage 65, 75 by means of hermetical contact of the sealing ring 65a, 75a with the inner wall of the valve sleeve 61, 71.

The adapter spigots 60 and 70 are coupled by the box-shaped coupling frame 80. Specifically, as shown in FIGS. 4 and 5, the box-shaped coupling frame 80 is in a shape of an open-bottomed housing is provided with a generally L-shaped stopper cover 82 for closing the open bottom of the housing. The coupling box frame 80 is provided with a spring guide projection 81 laterally projecting from an end wall and covered by the L-shaped stopper cover 82. In a space formed between the end wall of the coupling frame 80 and a bent end wall 82a of the stopper cover 82 there is provided with biasing means such as an expansion coil spring 83. The L-shaped stopper cover 82 has two circular access openings 84, each having a diameter greater than the possibly largest flange 46a of the valve mount 46 (see FIG. 3) of the air/water valve 40A or the suction valve 40B so that, when cleaning adapter unit 50 is attached to the control section 1 of the endoscope through insertion of the adapter spigots 60 and 70 into the air/water valve 40A and the suction valve 40B shown in FIG. 3, respectively, the stopper cover 82 allows the flanges 46a of the valve mounts 46 to pass through the access openings 84, respectively, and then, to force edges of the access openings 84 against side walls of the union nuts 45 in one direction.

As just described above, the cleaning adapter unit 50 is capable of connecting the cleaning device to two types of endoscopes having different fluid control valves, respectively. As shown by way of example, the cleaning adapter unit 50 shown in FIG. 5 is attached to an endoscope with the air/water valve 20 and the suction valve 30 shown in FIG. 2, and the cleaning adapter unit 50 shown in FIG. 6 is attached to an endoscope equipped with the air/water valve 40A and the suction valve 40B shown in FIG. 3.

An endoscope, equipped either with the air/water valve 20 and the suction valve 30 or equipped with the air/water valve 40A and the suction valve 40B, to which the cleaning adapter unit 50 is attached is quite easily handled as one whole.

The endoscope is generally cleaned by dipping not only the insertion section 2 but also the universal cord 3, and more preferably the whole endoscope including the connector 4, in a cleaning liquid, and besides, by rinsing interiors or passages of the instrument channel 10, the air supply tube 11, the water supply tube 12 and the suction tube 13 with a chemical liquid. In order to perform cleaning of the interior of the air supply tube 11 and the water supply tube 12 of the endoscope which has the air/water valve 20 and the suction valve 30 (shown in FIG. 2), after pulling out the valve body assemblies 22 and 33 together with the operating button 24 and 34 from the valve mounts 21a and 32a of the valve casings 21 and the valve guide sleeve 32, respectively, the cleaning adapter unit 50 is attached to the endoscope by snugly fitting the fitting end sections 68 and 78 of valve sleeves 61 and 71 of the adapter spigots 60 and 70 into the valve mounts 21a and 32a of the valve casing 21 and the valve guide sleeve 31, respectively, on the side of the endoscope. When gradually inserting the fitting end section 68, 78 of the valve sleeve 61, 71 until it abuts against the bottom of the valve mount 21a, 32a, the valve body 62, 72 is moved upward relatively to the valve sleeve 61, 71 and is finally put in the first position where the end of the of the valve sleeve 61, 71 abuts against a shoulder of the passage sleeve 65a, 75a as shown in FIG. 5. Consequentially, the second passage 65, 75 is brought into communication with the valve chamber 63, 73, and hence the first passage formed by the fluid introduction pipe 64, 74, and, on the other hand, shut off from the valve chamber 63, 73, and hence the first passage. Simultaneously, the second passage 65, 75 leads to the passages defined by the air supply tube 11 and the water supply tube 12 or the suction tube 13 through the valve casing 21, 31. In this way, the cleaning adapter unit 50 is completely attached to the endoscope. Thereafter, the cleaning adapter unit 50 is coupled to the cleaning device by connecting the fluid introduction pipes 64 and 74 to chemical supply pipes (not shown) of the cleaning device, respectively.

Cleaning chemicals, either the same as or different from each other, are fed under pressure into the valve chambers 63 and 73 of the adapter spigots 60 and 70, respectively, from the cleaning device through the fluid introduction pipes 64 and 74 through the fluid introduction pipes 64 and 74 (fist passages), respectively, and then, into the interiors or passages of the air supply tube 11, the water supply tube 12 and the suction tube 13 through the valve sleeves 2 1and 31 (second passages), respectively.

When attaching the cleaning adapter unit 50 to another endoscope equipped with the air/water valve 40A and the suction valve 40B different in mechanism and sizes from the air/water valve 20 and the suction valve 30, after detaching the cleaning adapter unit 50 from the endoscope equipped with the air/water valve 20 and the suction valve 30 (shown in FIG. 5) and, on the other hand, pulling out the valve body assemblies 43 together with the operating buttons 44 from the valve mounts 46 of the valve casings 42, respectively, the cleaning adapter unit 50 is turned upside down so that the third passages 66 and 76 of the adapter spigots 60 and 70 face the control section 1, more specifically the air/water valve 40A and the suction valve 40B, of the endoscope (shown in FIG. 3), respectively. Subsequently, the fitting end section 69, 79 of each valve body 62, 72 of the adapter spigot 60, 70 is snugly fitted into the valve mount 46 screwed in the valve casing 42 on the side of the endoscope. When gradually pushing down the box-shaped coupling frame 80 inserting the fitting end section 69, 79 until the fitting end section 69, 79 abuts against the bottom of the valve mount 46, the valve sleeve 61, 71 is moved down relatively to the valve body 62, 72 and finally put in the second position where the end of the of the valve sleeve 61, 71 abuts against the shoulder of the fitting end section 69, 79 as shown in FIG. 6. Consequentially, the third passage 66, 76 is brought into communication with the valve chamber 63, 73, and hence the first passage formed by the fluid introduction pipe 64, 74, and, on the other hand, the second passage 65, 75 is shut off from the valve chamber 63, 73, and hence the first passage. Simultaneously, the third passage 66, 76 leads to the passages defined by the air supply tube 11 and the water supply tube 12 or the suction tube (not shown n FIG. 3) through the valve casing 42. In this way, the cleaning adapter unit 50 is completely attached to the endoscope. For safety sake, the L-shaped stopper cover 82 is forced with expansion force of the coil spring 83 to slide in a direction in which the edges of the of the access openings 84 are brought into engagement with side walls of the union nuts 45. Thereafler, the cleaning adapter unit 50 is coupled to the cleaning device by connecting the fluid introduction pipes 64 and 74 to the chemical supply ports of the cleaning device.

In this instance, since the respective valve mounts on the side of the endoscopes have comparatively long fitting depths, and the sealing rings 61*a*, 71*a*, 67*b* and 77*b* are compressed and create resistance between the valve mounts and the valve sleeve or the valve guide sleeve when the adapter spigots 60 and 70 are sufficiently inserted, the cleaning adapter unit 50 is firmly held and does not slip off from the endoscope not only while feeding the air supply tube 11, the water supply tube 12 and the suction tube 13 with cleaning chemical liquids but while dipping the whole endoscope in a rinsing water.

It is to be understood that although the present invention has been described with regard to preferred embodiments thereof, various other embodiments and variants may occur to those skilled in the art, which are within the scope and spirit of the invention, and such other embodiments and variants are intended to be covered by the following claims.

What is claimed is:

1. A cleaning adapter unit for connecting cleaning fluid supply means selectively to either of a first or a second endoscope to supply cleaning fluid from said cleaning fluid supply means into respective conduits of said first or second endoscope, said first endoscope equipped with a first fluid control valve means comprised of a first valve casing and a first valve body removably received in said first valve casing and said second endoscope equipped with a second fluid control valve means comprised of a second valve casing different in shape from the first valve casing and a second valve body removably received in said second valve casing, said first and second valve casings connected to said conduits, said cleaning adapter unit comprising:

an adapter valve sleeve extending longitudinally with openings at opposing first and second ends, the adapter valve sleeve also having an inlet fluid passage detachably connectable to said cleaning fluid supply means, and a first fitting means at the first end of said adapter valve sleeve, said first fitting means being formed so as to be hermetically received in said first valve casing of said first endoscope; and an adapter valve body received in said adapter valve sleeve and slidable between a first position and a second position along a longitudinal direction between the first and second ends of the adapter valve sleeve, a first end of the adapter valve body corresponding to the first end of the adapter valve sleeve and a second end of the adapter valve body corresponding to the second end of the adapter valve sleeve, the adapter valve body and the adapter valve sleeve forming a valve chamber connected to said inlet fluid passage when said adapter valve sleeve is in either of said first or second positions, said adapter valve body provided with a first fluid passage with an opening at the first end of said adapter valve body, the first fluid passage in fluid connection with said valve chamber when said adapter valve sleeve is in said first position, and a second fluid passage forming an opening at the second end of said adapter valve body, the opening at the second end of said adapter valve body facing opposite the opening at the first end of said adapter valve body, and the second fluid passage in fluid connection with said valve chamber when said adapter valve sleeve is in said second position, and said adapter valve body further provided with a second fitting means at the second end of the adapter valve body, said second fitting means being formed so as to be hermetically received in said second valve casing of said second endoscope, wherein said first and second fitting means are different in shape from each other such that said first fitting means is configured to tightly fit into said first valve casing of said first endoscope and the second fitting means is configured to tightly fit into said second valve casing of the second endoscope, wherein said adapter valve body is configured to slide to said first position when said cleaning adapter unit is attached to said first endoscope by fitting said first fitting means into said first valve casing of said first endoscope, and wherein said adapter valve body is configured to slide to said second position when said cleaning adapter unit is attached to said second endoscope by fitting said second fitting means into said second valve casing of said second endoscope.

2. The cleaning adapter unit of claim 1, wherein said cleaning adapter unit comprises two of said adapter valve sleeves and two of said adapter valve bodies, each adapter valve sleeve receiving one of said adapter valve bodies, and wherein said cleaning adapter unit further comprises coupling means for coupling said adapter valve sleeves side by side at a predetermined distance.

3. The cleaning adapter unit of claim 2, wherein said coupling means comprises i) a coupling frame for fixedly coupling said adapter valve sleeves side by side, ii) a stopper cover having a circular access opening for receiving a flanged portion of said second valve casing of said second endoscope, the stopper cover being slidably attached to said coupling frame, and iii) biasing means disposed between said coupling frame and said stopper cover for biasing said stopper cover in a direction for bringing said stopper cover into engagement with said flanged portion at an edge of said access opening.

4. The cleaning adapter unit of claim 1, wherein the adapter valve body is configured to slide bi-directionally between the first and second positions within the adapter valve sleeve along an axis running between the opposite first and second ends of the adapter valve sleeve.

5. The cleaning adapter unit of claim 4 in combination with one of the first and second endoscopes, the first fitting means hermetically received in the first valve casing of said first endoscope and the adapter valve body in the first position with respect to the adapter valve sleeve in a first mode, and the second fitting means hermetically received in the second valve casing of said second endoscope and the adapter valve body in a second position with respect to the adapter valve sleeve in the second mode, the second position being different from the first position, wherein in the first mode, the second fitting means is free of a connection to the second endoscope, and wherein in the second mode, the first fitting means is free of a connection to the first endoscope.

6. The cleaning adapter unit of claim 1 in combination with one of the first and second endoscopes, the first fitting means hermetically received in the first valve casing of said first endoscope in a first mode, and the second fitting means hermetically received in the second valve casing of said second endoscope in a second mode, wherein, in the first mode, the second fitting means is free of a connection to the second endoscope, and wherein, in the second mode, the first fitting means is free of a connection to the first endoscope.

7. The cleaning adapter unit of claim 1, wherein in said first position, said adapter valve body cooperates with said adapter valve sleeve to shut off fluid communication between the second fluid passage and said valve chamber, and wherein in said second position, said adapter valve body cooperates with said adapter valve sleeve to shut off fluid communication between the first fluid passage and said valve chamber.

8. A cleaning adapter unit for connecting a cleaning fluid supply to either of a first endoscope or a second endoscope different from said first endoscope, said cleaning adapter unit comprising:

an adapter valve sleeve having an inlet fluid passage detachably connectable to said cleaning fluid supply and having opposing first and second ends;

an adapter valve body disposed in said adapter valve sleeve and forming a valve chamber in the adapter valve sleeve, said adapter valve body being slidably movable inside said adapter valve sleeve between said first and second ends of the adapter valve sleeve;

a first fitting positioned at the first end of said adapter valve sleeve and adapted to be hermetically received in a first valve casing of said first endoscope;

a second fitting positioned at an end of said adapter valve body and facing opposite the first end of said adapter valve sleeve and adapted to be hermetically received in a second valve casing, different in shape from the first valve casing, of said second endoscope different in type from the first endoscope; and first and second fluid passages separately disposed inside said adapter valve body, said first and second fluid passages having respective openings facing opposite directions at the first end of said adapter valve body and an opposing second end of said adapter valve body, wherein said adapter valve body, in a first mode, slides to a first position with respect to the adapter valve sleeve to enable said first fitting to attach to the first valve casing of said first endoscope so that said first fluid passage is in fluid connection with said inlet fluid passage through said valve chamber to supply a cleaning fluid from said cleaning fluid supply to the first fitting and into at least one conduit connected to said second valve casing of said first endoscope, and wherein said adapter valve body, in a second mode, slides to a second position with respect to the adapter valve sleeve to enable said second fitting to attach to the second valve casing of said second endoscope so that said second fluid passage is in fluid connection with said inlet fluid passage through said valve chamber to supply the cleaning fluid from said cleaning fluid supply to the second fitting and into at least one conduit connected to said second valve casing of said second endoscope.

9. The cleaning adapter unit of claim 8, wherein said cleaning adapter unit comprises two of said adapter valve sleeves and two of said adapter valve bodies, each adapter valve sleeve receiving one of said adapter valve bodies, and wherein said cleaning adapter unit further comprises coupling means for coupling said adapter valve sleeves side by side at a predetermined distance.

10. The cleaning adapter unit of claim 8 in combination with one of the first and second endoscopes, the first fitting hermetically received in the first valve casing of said first endoscope in the first mode, and the second fitting hermetically received in the second valve casing of said second endoscope in the second mode, wherein in the first mode, the second fitting is free of a connection to the second endoscope, and wherein in the second mode, the first fitting is free of a connection to the first endoscope.

11. The cleaning adapter unit of claim 8, wherein in said first mode, said adapter valve body cooperates with said adapter valve sleeve to shut off fluid communication between said second fluid passage and said inlet fluid passage, and wherein in said second mode, said adapter valve body cooperates with said adapter valve sleeve to shut off fluid communication between said first fluid passage and said inlet fluid passage.

* * * * *